United States Patent [19]

Bernardi et al.

[11] Patent Number: 4,500,712
[45] Date of Patent: Feb. 19, 1985

[54] ERGOLINE DERIVATIVES

[75] Inventors: Luigi Bernardi; Aldemio Temperilli; Daniela Ruggieri; Giuliana Arcari; Patricia Salvati, all of Milan, Italy

[73] Assignee: Farmitalia Carlo Erba S.p.A., Milan, Italy

[21] Appl. No.: 438,259

[22] Filed: Nov. 1, 1982

[30] Foreign Application Priority Data

Nov. 6, 1981 [GB] United Kingdom ................ 8133631

[51] Int. Cl.³ .................. C07D 457/04; A61K 31/48
[52] U.S. Cl. .......................................... 546/67; 546/68
[58] Field of Search .................... 548/67, 69; 424/261

[56] References Cited

U.S. PATENT DOCUMENTS

| | | | |
|---|---|---|---|
| 3,717,640 | 2/1973 | Arcari et al. | 424/261 |
| 3,732,231 | 5/1973 | Semonsky et al. | 424/261 |
| 3,821,226 | 6/1974 | Fehr et al. | 546/67 |
| 3,966,941 | 6/1976 | Semonsky et al. | 424/261 |
| 4,201,862 | 5/1980 | Kornfeld et al. | 424/261 |
| 4,235,912 | 11/1980 | Rettegi et al. | 424/261 |

FOREIGN PATENT DOCUMENTS

| | | | |
|---|---|---|---|
| 753602 | 1/1971 | Belgium | 546/67 |
| 71563 | 2/1983 | European Pat. Off. | 424/261 |
| 1005880 | 9/1965 | United Kingdom | 424/261 |

*Primary Examiner*—Mark L. Berch
*Assistant Examiner*—G. Hendricks
*Attorney, Agent, or Firm*—Oblon, Fisher, Spivak, McClelland & Maier

[57] ABSTRACT

There are provided ergoline derivatives of formula

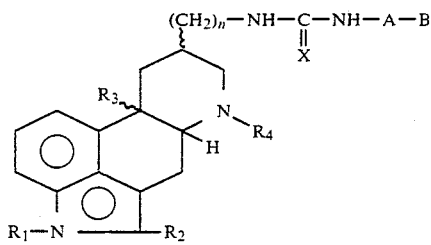

wherein $R_1$=H, $CH_3$; $R_2$=H or halogen atom, or $CH_3$, CN, alkyl- or phenyl-thio; $R_3$=H, $OCH_3$; $R_4$=$C_1$-$C_4$ hydrocarbon group; X=O, S, NH; A=CO, $SO_2$; B=$C_1$-$C_4$ hydrocarbon group, aryl, aralkyl, heterocyclic ring group, alkoxy, aryloxy; n=0, 1, 2; and pharmaceutically acceptable salts thereof.

A process for preparing said compounds is also provided. The compounds show anti-hypertensive activity and are active on the gastroenteric system.

3 Claims, No Drawings

ERGOLINE DERIVATIVES

This invention provides ergoline derivatives having the general formula I

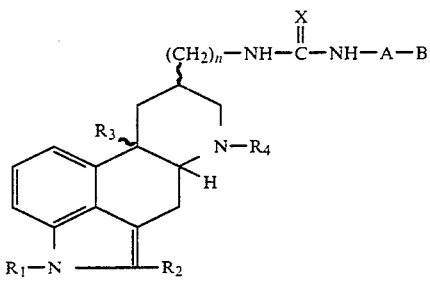

wherein
R₁ represents a hydrogen atom or a methyl group;
R₂ represents a hydrogen or halogen atom or a methyl, cyano, lower alkylthio or phenylthio group;
R₃ represents a hydrogen atom or a methoxy group;
R₄ represents a hydrocarbon group having from 1 to 4 carbon atoms;
X represents an oxygen or sulphur atom or an imino group;
A represents a carbonyl or sulphonyl group;
B represents a hydrocarbon group having from 1 to 4 carbon atoms, a substituted or unsubstituted aryl, aralkyl or 5- or 6-membered heterocyclic ring group, or lower alkoxy or aryloxy group; and
n is 0, 1 or 2.

The invention further provides pharmaceutically acceptable salts of such ergoline derivatives.

In the definitions of formula I, the term "halogen" should be construed as preferably encompassing chlorine and bromine atoms; nevertheless, the term "halogen" also encompasses the fluorine atom.

The term "lower alkyl" encompasses alkyl groups having from 1 to 4 carbon atoms; in particular methyl, ethyl, n-propyl, isopropyl, butyl, t-butyl, iso-butyl.

In the definitions of R₄ and B, a hydrocarbon group having from 1 to 4 carbon atoms is intended to include alkyl, cycloalkyl and unsaturated (both ethylenically and acetylenically) groups.

Representative moieties include the above listed lower alkyl or allyl, propargyl and methylcyclopropyl groups.

In the definition of B, the aralkyl group is, especially, a benzyl group; the term "aryl" preferably encompasses phenyl and the 5–6 membered heterocyclic ring preferably containing at least one heteroatom selected from the group consisting of N, S and O.

The heterocyclic ring may be, for example, triazolyl, tetrazolyl, imidazolyl, pyrrolyl, pyridyl, pyrimidyl, pyrazinyl, and pyridazinyl.

When B is a substituted aryl, aralkyl or heterocyclic ring group, the substituent is, preferably, a lower alkyl group, lower alkoxy, a halogen atom or a nitro group.

Particularly preferred compounds according to this invention are indicated hereinafter:
6-methyl-8α-(3-benzoyl-thioureidomethyl)-10β-ergoline,
6-methyl-8β-(3-benzoyl-thioureidomethyl)-ergoline,
6-methyl-8β-(3-acetyl-thioureidomethyl)-ergoline,
6-methyl-8β-(3-propionyl-thioureidomethyl)-ergoline,
6-methyl-8α(3-benzoyl-thioureidomethyl)-ergoline,
6-methyl-8β-(3-benzoyl-thioureido)-ergoline,
6-methyl-8α(3-benzoyl-ureidomethyl)-10β-ergoline,
6-methyl-8β-(3-benzoyl-ureidomethyl)-ergoline,
6-methyl-8β-(3-acetyl-ureidomethyl)-ergoline,
6-methyl-8α-(3-benzoyl-ureidomethyl)-ergoline,
6-methyl-8β-(3-benzoyl-ureido)-ergoline,
6-methyl-8β-(3-acetyl-ureido)-ergoline,
6-methyl-8β-(3-benzoyl-thioureidoethyl)-ergoline,
6-methyl-8β-(3-acetyl-thioureidoethyl)-ergoline,
6-methyl-8β-(3-benzoyl-ureidoethyl)-ergoline,
6-methyl-8β-(3-acetyl-thioureido)-ergoline,
6-methyl-8β-(3-benzoyl-guanidinomethyl)-ergoline,
6-methyl-8β-(3-acetyl-guanidinomethyl)-ergoline,
1,6-dimethyl-8β-(3-acetyl-thioureidomethyl)-ergoline,
1,6-dimethyl-8β-(3-nicotinoyl-guanidinomethyl)-ergoline,
1,6-dimethyl-8β-3-(5-bromonicotinoyl)-guanidino methyl-ergoline,
6-methyl-8β-(3-p-toluensulfonyl-ureidomethyl)-ergoline,
10-methoxy-6-methyl-8β-(3-acetyl-thioureidomethyl)-ergoline,
10-methoxy-1,6-dimethyl-8β-(3-acetyl-thioureidomethyl)-ergoline,
6-methyl-8α-(3-acetyl-thioureidomethyl)-ergoline,
6-methyl-8α-(3-acetyl-ureidomethyl)-ergoline,
6-propyl-8β-(3-benzoyl-ureidoethyl)-ergoline,
6-allyl-8β-(3-benzoyl-ureidoethyl)-ergoline,
2,6-dimethyl-8β-(3-acetyl-ureidomethyl)-ergoline and
2-bromo-6-methyl-8β-(3-acetyl-ureidomethyl)-ergoline.

The invention further provides a process for the preparation of ergoline derivatives of the general formula I as herein defined, the process comprising reacting an ergoline amine of the general formula II

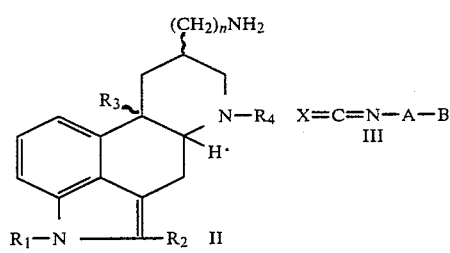

with an isocyanate, an isothiocyanate or an isoiminocyanate of formula III wherein R₁, R₂, R₃, R₄, X, A, B and n are as above defined.

The condensation process is preferably carried out in an organic solvent such as acetonitrile, dioxan or toluene, at room temperature or at the boiling temperature of the solvent for a period of from 0.5 to 2 hours.

When the reaction is over, the crude product may be purified by crystallization or by chromatography.

The ergoline amines of formula II, the starting materials for the process, are known compounds or can be prepared by reducing the corresponding 8-carbamoyl-(alkyl)-ergolines with lithium and aluminum hydride, as described in U.S. Pat. No. 3,238,211.

The ergoline derivatives according to the present invention and their pharmaceutically acceptable salts exhibit from moderate-to-good antihypertensive activity and are active on the gastroenteric system. In particular, they are endowed with antiulcerogenic, anti-secretory and a very negligible anticholinergic activity and are therefore useful in therapy, for example in the prevention and treatment of peptic, e.g. duodenal, gastric and exophagal ulcers and to inhibit gastric acid secretion.

The administration of compounds I and their non-toxic, pharmaceutically acceptable acid addition salts or mixtures thereof may be achieved either parenterally or orally. Typically, an effective amount of the derivative is combined with a suitable pharmaceutical carrier.

As used herein, the term "effective amount" encompasses those amounts which yield the desired activity without causing adverse side effects.

The pharmaceutical carriers which are typically employed with the compounds of the invention may be solid or liquid and are generally selected dependent on the planned manner of administration. Thus, for example, solid carriers include lactose, sucrose, gelatin and agar and the like, while liquid carriers include water, syrup, peanut oil and olive oil and the like. The combination of the selected compound and the carrier may be fashioned into numerous acceptable forms such as tablets, capsules, suppositories, solutions, emulsions, powders and syrups.

EVALUATION OF ACTIVITY ON THE GASTRO-ENTERIC SYSTEM

The anti-ulcerogenic activity of the compounds of the present invention is shown, e.g., by the fact that they are active in the test of the inhibition of restraint ulcers in rats, according to the method of Bonfils et al., (Therapie, 1960, 15, 1096). According to this method the tested compounds were administered per os one hour before the immobilization.

Six Sprague-Dawley male rats (100–120 g), fasted 24 hours, were used for the experiment: a square flexible small-mesh wire netting was used for the immobilization and 4 hours after the immobilization the rats were sacrificed, their stomachs were removed and the lesions counted under a dissecting microscope.

The compounds of the present invention also display gastric antisecretory activity as shown e.g. by the fact that they proved to be active after intraduodenal administration in inhibiting the gastric secretion in rats according to the method of H. Shay et al. (Gastroenter. 1945, 43, 5). According to this method the tested compounds were injected intraduodenally at the time of ligature. Six Sprague-Dawley male rats (110–130 g) were used for each group. Twenty-four hours before the test, the rats were deprived of food but the water supply was maintained. On the day of the operation, the pylorus was ligated under light ether anaesthesia. Four hours after the ligature, the rats were sacrificed. The stomach secretion was collected and centrifuged at 3500 r.p.m. for 10 minutes and the volume, less sediment, was determined. The amount of free hydrochloric acid in the gastric juice was determined by titration against 0.01N sodium hydroxide, to an end point of pH 7.

Table 1 shows the $ED_{50}$ values of the anti-ulcerogenic activity (oral administration) and antisecretory activity (intraduodenal administration) in the rat obtained from compounds of the present invention.

TABLE 1

| Compound | Anticular activity ($ED_{50}$, mg/kg p.o.) | Antisecretory activity ($ED_{50}$, mg/kg i.d.) |
| --- | --- | --- |
| 6-methyl-8β-(3-benzoylthioureidomethyl)-ergoline (Ex 2) | 0.7 | 1.4 |
| 6-methyl-8α-(3-benzoylthioureidomethyl)-10β-ergoline (Ex 1) | 4.2 | 2.5 |
| 6-methyl-8α-(3-benzoylureidomethyl)-ergoline (Ex 10) | 7 | 1 |

Considering that many anti-ulcer agents display, as atropine does, a remarkable but undesired anti-cholinergic activity, the compounds of the present invention were also assessed for their antagonism against syndrome induced by oxotremorine in mice, according to the method described by Leszkovsky G. P. and Tardos L. (Europ. J. Pharmac. 1971, 15, 310). According to this method 5 male mice, 20–25 g body weight, were used for each group. The results obtained show that compounds of the present invention are devoid of anticholinergic effect up until a dose of 100 mg/kg p.o.

EVALUATION OF THE ANTIHYPERTENSIVE ACTIVITY

Indirect measurements of systolic blood pressure were carried out on groups of 4 spontaneously hypertensive rats (SHR, Kyoto), 8–10 weeks of age, supplied by Charles Rives, Italy.

The animals were maintained in an environment of 36° C. for 10–15 minutes to allow pulse pressure to be recorded and then systolic blood pressure and heart rate were measured by indirect tail cuff method using a W+W, BP recorder, model 8005.

The compounds were given orally, suspended in 5% arabic gum, once a day for 4 consecutive days and measurements were carried out before beginning the treatment and 1 and 5 hours after dosing in both the first and fourth day of treatment.

Control animals received the vehicle only (0.2 ml/100 g b.w.). As reference standards, hydralazine (1–5 mg/kg p.o.) and α-methyl-dopa (30–100 mg/kg p.o.) were also tested.

Drug-induced changes in systolic blood pressure and heart rate were calculated as differences from the pretreatment values.

TABLE 2

Effect on systolic blood pressure (S.B.P.) in SH-rats. Mean differences from pretreatment values (mmHg) are reported (4 rats per group).

| | | Changes in S.B.P ($\Delta$mmHg) | | | |
| --- | --- | --- | --- | --- | --- |
| | | 1st day | | 4th day | |
| Compound | Dose (mg/kg p.o.) | 1 h post drug | 5 h post drug | 1 h post drug | 5 h post drug |
| 6-methyl-8β-(3-acetyl-thioureidomethyl)-ergoline (Ex 3) | 5 | −22 | −36 | −16 | −40 |
| 6-methyl-8β-(3-acetyl-ureidomethyl)-ergoline (Ex 9) | 5 | −25 | −17 | −57 | −56 |
| 6-methyl-8α-(3-acetyl-ureidomethyl)-ergoline (Ex 26) | 5 | −28 | −60 | −45 | −36 |
| Hydralazine | 1 | −5 | −15 | −5 | 0 |
| | 5 | −40 | −20 | −20 | −7 |
| α-methyl-DOPA | 30 | −10 | −20 | −10 | 0 |

TABLE 2-continued

Effect on systolic blood pressure (S.B.P.) in SH-rats.
Mean differences from pretreatment values (mmHg) are reported
(4 rats per group).

| Compound | Dose (mg/kg p.o.) | Changes in S.B.P ($\Delta$mmHg) | | | |
|---|---|---|---|---|---|
| | | 1st day | | 4th day | |
| | | 1 h post drug | 5 h post drug | 1 h post drug | 5 h post drug |
| | 100 | −10 | −25 | −20 | −25 |

TABLE 3

Effects on heart rate (HR) in SH-rats. Mean differences from pretreatment values (beats/min) are reported (4 rats per group).

| Compound | Dose (mg/kg p.o.) | Changes in HR (beats/min) | | | |
|---|---|---|---|---|---|
| | | 1st day | | 4th day | |
| | | 1 h post drug | 5 h post drug | 1 h post drug | 5 h post drug |
| 6-methyl-8α-(3-acetyl-thioureidomethyl)-ergoline (Ex 3) | 5 | −10 | −20 | −15 | −21 |
| 6-methyl-8β-(3-acetyl-ureidomethyl)-ergoline (Ex 9) | 5 | +10 | −15 | −17 | −22 |
| 6-methyl-8α-(3-acetyl-ureidomethyl)-ergoline (Ex 26) | 5 | +5 | +8 | +9 | +10 |
| Hydralazine | 1 | +30 | +35 | +25 | +15 |
| | 5 | +40 | +45 | +18 | +15 |
| α-methyl-DOPA | 30 | +35 | +40 | +45 | +30 |
| | 100 | +70 | +40 | +50 | +10 |

From the data reported in Table 2, the compounds according to the present invention induce a consistent systolic blood pressure decrease in spontaneously hypertensive rats.

This reduction of the blood pressure appears not only on the first day of treatment but also on the fourth day showing that tolerance does not occur. When compared with hydralazine and α-methyl-DOPA the new compounds, at the dose of 5 mg/kg, show a greater hypotensive effect—particularly on the fourth day.

Considering the effects on heart rate (HR), it can be seen (Table 3) that the new compounds do not increase HR, as hydralazine and α-methyl-DOPA do, but, on the contrary, induce moderate bradycardia.

The following examples still further illustrate the invention:

EXAMPLE 1

6-Methyl-8α-(3-benzoyl-thioureidomethyl)-10β-ergoline
($R_1=R_2=R_3=H$; $R_4=CH_3$; $X=S$; $A=CO$; $B=C_6H_5$; n=1)

1.05 ml of benzoyl isothiocyanate were added to a suspension of 2 g of 8α-aminomethyl-6-methyl-10β-ergoline in 22 ml of acetonitrile at 80° C. under shaking. The solution was refluxed for thirty minutes and then evaporated in vacuo to dryness. The residue was chromatographed on silica gel (eluant chloroform with 2% methanol) to give 2.2 g of the title compound, m.p. 153°–155° C., after crystallization from diethyl ether.

EXAMPLE 2

6-Methyl-8β-(3-benzoyl-thioureidomethyl)-ergoline
($R_1=R_2=R_3=H$; $R_4=CH_3$; $X=S$; $A=CO$; $B=C_6H_5$; n=1)

Operating as in Example 1, but employing 8β-aminomethyl-6-methyl-ergoline in place of 8α-aminomethyl-6-methyl-10β-ergoline, the title compound, m.p. 236°–237° C., was obtained in 70% yield.

EXAMPLE 3

6-Methyl-8β-(3-acetyl-thioureidomethyl)-ergoline
($R_1=R_2=R_3=H$; $R_4=B=CH_3$; $X=S$; $A=CO$; n=1)

Operating as in Example 2, but employing acetyl isothiocyanate in place of benzoyl isothiocyanate and toluene in place of acetonitrile, the title compound, m.p. 209°–210° C., was obtained in 55% yield.

EXAMPLE 4

6-Methyl-8β-(3-propionyl-thioureidomethyl)-ergoline
($R_1=R_2=R_3=H$; $R_4=CH_3$; $X=S$; $A=CO$; $B=C_2H_5$; n=1)

Operating as in Example 2, but employing propionyl isothiocyanate in place of benzoyl isothiocyanate and dioxan in place of acetonitrile, the title compound, m.p. 225°–226° C., was obtained in 58% yield.

EXAMPLE 5

6-Methyl-8α-(3-benzoyl-thioureidomethyl)-ergoline
($R_1=R_2=R_3=H$; $R_4=CH_3$; $X=S$; $A=CO$; $B=C_6H_5$; n=1)

Operating as in Example 1, but employing 8α-aminomethyl-6-methyl-ergoline in place of 8α-aminomethyl-6-methyl-10β-ergoline, the title compound was obtained in 65% yield, m.p. 155°–156° C.

EXAMPLE 6

6-Methyl-8β-(3-benzoyl-thioureido)-ergoline
($R_1=R_2=R_3=H$; $R_4=CH_3$; $X=S$; $A=CO$; $B=C_6H_5$; n=0)

Operating as in Example 1, but employing 8β-amino-6-methyl-ergoline in place of 8α-aminomethyl-6-methyl-10β-ergoline, the title compound was obtained in 70% yield, m.p. 224°–225° C.

EXAMPLE 7

6-Methyl-8α-(3-benzoyl-ureidomethyl)-10β-ergoline
($R_1=R_2=R_3=H$; $R_4=CH_3$; $X=O$; $A=CO$; $B=C_6H_5$; n=1)

Operating as in Example 1, but employing benzoyl isocyanate in place of benzoyl isothiocyanate, the title compound was obtained in 64% yield, m.p. 142°–144° C.

EXAMPLE 8

6-Methyl-8β-(3-benzoyl-ureidomethyl)-ergoline
($R_1=R_2=R_3=H$; $R_4=CH_3$; $X=O$; $A=CO$; $B=C_6H_5$; n=1)

Operating as in Example 2, but employing benzoyl isocyanate in place of benzoyl isothiocyanate, the title compound was obtained in 73% yield, m.p. 180°–181° C.

EXAMPLE 9

6-Methyl-8β-(3-acetyl-ureidomethyl)-ergoline
($R_1=R_2=R_3=H$; $R_4=B=CH_3$; $X=O$; $A=CO$; n=1)

Operating as in Example 2, but employing acetyl isocyanate in place of benzoyl isothiocyanate, the title compound was obtained in 65% yield, m.p. 256°–257° C.

EXAMPLE 10

6-Methyl-8α-(3-benzoyl-ureidomethyl)-ergoline
($R_1=R_2=R_3=H$; $R_4=CH_3$; $X=O$; $A=CO$; $B=C_6H_5$; $n=1$)

Operating as in Example 5, but employing benzoyl isocyanate in place of benzoyl isothiocyanate, the title compound was obtained in 70% yield, m.p. 190°–191° C.

EXAMPLE 11

6-Methyl-8β-(3-benzoyl-ureido)-ergoline
($R_1=R_2=R_3=H$; $R_4=CH_3$; $X=O$; $A=CO$; $B=C_6H_5$; $n=0$)

Operating as in Example 6, but employing benzoyl isocyanate in place of benzoyl isothiocyanate, the title compound was obtained in 74% yield, m.p. 239°–241° C.

EXAMPLE 12

6-Methyl-8β-(3-acetyl-ureido)-ergoline
($R_1=R_2=R_3=H$; $R_4=B=CH_3$; $X=O$; $A=CO$; $n=0$)

Operating as in Example 6, but employing acetyl isocyanate in place of benzoyl isothiocyanate, the title compound was obtained in 54% yield, m.p. 237°–239° C.

EXAMPLE 13

6-Methyl-8β-(3-benzoyl-thioureidoethyl)-ergoline
($R_1=R_2=R_3=H$; $R_4=CH_3$; $X=S$; $A=CO$; $B=C_6H_5$; $n=2$)

Operating as in Example 1, but employing 8β-aminoethyl-6-methyl-ergoline in place of 8α-aminomethyl-6-methyl-10β-ergoline, the title compound, m.p. 205°–207° C., was obtained in 85% yield.

EXAMPLE 14

6-Methyl-8β-(3-acetyl-thioureidoethyl)-ergoline
($R_1=R_2=R_3=H$; $R_4=B=CH_3$; $X=S$; $A=CO$; $n=2$)

Operating as in Example 13, but employing acetyl isothiocyanate in place of benzoyl isothiocyanate, the title compound, m.p. 213°–215° C., was obtained in 78% yield.

EXAMPLE 15

6-Methyl-8β-(3-benzoyl-ureidoethyl)-ergoline
($R_1=R_2=R_3=H$; $R_4=CH_3$; $X=O$; $A=CO$; $B=C_6H_5$; $n=2$)

Operating as in Example 13, but employing benzoylisocyanate in place of benzoyl isothiocyanate, the title compound, m.p. 215°–217° C., was obtained in 72% yield.

EXAMPLE 16

6-Methyl-8β-(3-acetyl-thioureido)-ergoline
($R_1=R_2=R_3=H$; $R_4=B=CH_3$; $X=S$; $A=CO$; $n=0$)

Operating as in Example 6, but employing acetyl isothiocyanate in place of benzoyl isothiocyanate, the title compound, m.p. 240°–242° C., was obtained in 68% yield.

EXAMPLE 17

6-Methyl-8β-(3-benzoyl-guanidinomethyl)-ergoline
($R_1=R_2=R_3=H$; $R_4=CH_3$; $X=NH$; $A=CO$; $B=C_6H_5$; $n=1$)

Operating as in Example 2, but employing benzoyl cyanamide in place of benzoyl isothiocyanate the title compound, m.p. 190°–191° C., was obtained in 64% yield.

EXAMPLE 18

6-Methyl-8β-(3-acetyl-guanidinomethyl)-ergoline
($R_1=R_2=R_3=H$; $R_4=B=CH_3$; $X=NH$; $A=CO$; $n=1$)

Operating as in Example 2, but employing acetyl cyanamide in place of benzoyl isothiocyanate the title compound, m.p. 218°–220° C., was obtained in 58% yield.

EXAMPLE 19

1,6-Dimethyl-8β-(3-acetyl-thioureidomethyl)-ergoline
($R_2=R_3=H$; $R_1=R_4=B=CH_3$; $X=S$; $A=CO$; $n=1$)

Operating as in Example 3, but employing 8β-aminomethyl-1,6-dimethyl-ergoline in place of 8β-aminomethyl-6-methyl-ergoline, the title compound, m.p. 195°–197° C., was obtained in 70% yield.

EXAMPLE 20

1,6-Dimethyl-8β-(3-nicotinoyl-guanidinomethyl)-ergoline
($R_2=R_3=H$; $R_1=R_4=CH_3$; $X=NH$; $A=CO$; $B=3-C_5H_4N$, $n=1$)

Operating as in Example 19, but employing nicotinoyl cyanamide in place of acetyl isothiocyanate, the title compound, m.p. 207°–209° C., was obtained in 48% yield.

EXAMPLE 21

1,6-Dimethyl-8β-[3-(5-bromonicotinoyl)-guanidino methyl]-ergoline
($R_2=R_3=H$; $R_1=R_4=CH_3$; $X=NH$; $A=CO$; $B=5-Br-3-C_5H_3N$; $n=1$)

Operating as in Example 19, but employing 5-bromonicotinoyl cyanamide in place of acetyl isothiocyanate, the title compound, m.p. 140°–142° C., was obtained in 55% yield.

EXAMPLE 22

6-Methyl-8β-(3-p-toluensulfonyl-ureidomethyl)-ergoline
($R_1=R_2=R_3=H$; $R_4=CH_3$; $X=O$; $A=SO_2$; $B=4-CH_3-C_6H_4$; $n=1$)

Operating as in Example 2, but employing p-toluenesulfonyl isocyanate in place of benzoyl isothiocyanate, the title compound, m.p. 234°–236° C., was obtained in 73% yield.

EXAMPLE 23

10-Methoxy-6-methyl-8β-(3-acetyl-thioureidomethyl)-ergoline
($R_1=R_2=H$; $R_3=OCH_3$; $R_4=B=CH_3$; $X=S$; $A=CO$; $n=1$)

Operating as in Example 3, but employing 8β-aminomethyl-10-methoxy-6-methyl-ergoline in place of 8β-aminomethyl-6-methyl-ergoline, the title compound, m.p. 212°–214° C., was obtained in 75% yield.

EXAMPLE 24

10-Methoxy-1,6-dimethyl-8β-(3-acetyl-thioureidomethyl)-ergoline
($R_2=H$; $R_3=OCH_3$; $R_1=R_4=B=CH_3$; $X=S$; $A=CO$; $n=1$)

Operating as in Example 3, but employing 8β-aminomethyl-10-methoxy-1,6-dimethyl-ergoline in place of 8β-aminomethyl-6-methyl-ergoline, the title compound, m.p. 170°–172° C., was obtained in 73% yield.

EXAMPLE 25

6-Methyl-8α-(3-acetyl-thioureidomethyl)-ergoline
($R_1=R_2=R_3=H$; $R_4=B=CH_3$; $X=S$; $A=CO$; n=1)

Operating as in Example 5, but employing acetyl isothiocyanate in place of benzoyl isothiocyanate, the title compound, m.p. 204°–205° C., was obtained in 71% yield.

EXAMPLE 26

6-Methyl-8α-(3-acetyl-ureidomethyl)-ergoline
($R_1=R_2=R_3=H$; $R_4=B=CH_3$; $X=O$; $A=CO$; n=1)

Operating as in Example 5, but employing acetyl isocyanate in place of benzoyl isothiocyanate, the title compound, m.p. 182°–183° C., was obtained in 70% yield.

EXAMPLE 27

6-Propyl-8β-(3-benzoyl-ureidoethyl)-ergoline
($R_1=R_2=R_3=H$; $R_4=nC_3H_7$; $X=O$; $A=CO$; $B=C_6H_5$; n=2)

Operating as in Example 8, but employing 8β-aminoethyl-6-propyl-ergoline in place of 8β-aminomethyl-6-methyl-ergoline, the title compound, m.p. 194°–196° C., was obtained in 71% yield.

EXAMPLE 28

6-Allyl-8β-(3-benzoyl-ureidoethyl)-ergoline
($R_1=R_2=R_3=H$; $R_4=CH_2-CH=CH_2$; $X=O$; $A=CO$; $B=C_6H_5$; n=2)

Operating as in Example 8, but employing 8β-aminoethyl-6-allyl-ergoline in place of 8β-aminomethyl-6-methyl-ergoline, the title compound, m.p. 173°–175° C., was obtained in 64% yield.

EXAMPLE 29

2,6-Dimethyl-8β-(3-acetyl-ureidomethyl)-ergoline
($R_1=R_3=H$; $R_2=R_4=B=CH_3$; $X=O$; $A=CO$; n=1)

Operating as in Example 9, but employing 8β-aminomethyl-2,6-dimethyl-ergoline in place of 8β-aminomethyl-6-methyl-ergoline, the title compound, m.p. 275°–277° C., was obtained in 69% yield.

EXAMPLE 30

2-Bromo-6-methyl-8β-(3-acetyl-ureidomethyl)-ergoline
($R_1=R_3=H$; $R_2=Br$; $R_4=B=CH_3$; $X=O$; $A=CO$; n=1)

Operating as in Example 9, but employing 8β-aminomethyl-2-bromo-6-methyl-ergoline in place of 8β-aminomethyl-6-methyl-ergoline, the title compound, m.p. 210°–212° C., was obtained in 73% yield.

What is claimed is:

1. The compound 6-methyl-8β-(3-acetylthio-ureidomethyl)-ergoline having the formula:

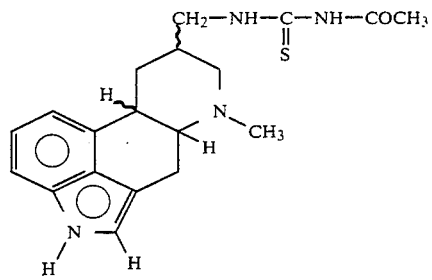

2. The compound 6-methyl-8β-(3-benzoyl-thioureidomethyl)-ergoline having the formula:

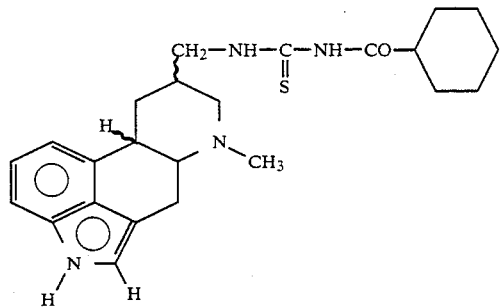

3. The compound 6-methyl-8β-(3-acetyl-ureidomethyl)-ergoline having the formula:

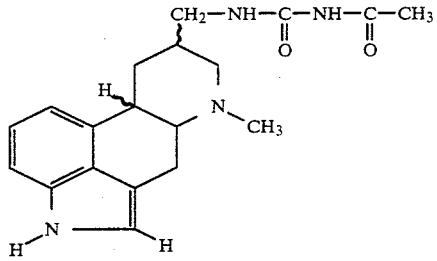

* * * * *

UNITED STATES PATENT AND TRADEMARK OFFICE
CERTIFICATE OF CORRECTION

PATENT NO. : 4,500,712
DATED : February 19, 1985
INVENTOR(S) : LUIGI BERNARDI ET AL Page 1 of 3

It is certified that error appears in the above-identified patent and that said Letters Patent is hereby corrected as shown below:

Column 4, line 2, delete "Anticular", and insert therefor

-- Antiulcer --.

Claim 1, delete the structure shown, and insert therefor

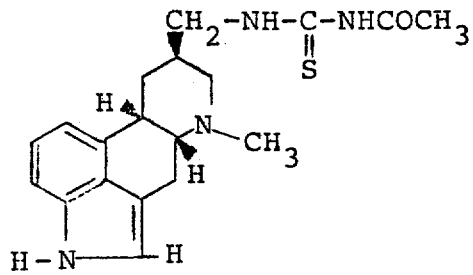

UNITED STATES PATENT AND TRADEMARK OFFICE
CERTIFICATE OF CORRECTION

PATENT NO. : 4,500,712
DATED : February 19, 1985
INVENTOR(S) : LUIGI BERNARDI ET AL It is certified that error appears in the above-identified patent and that said Letters Patent is hereby corrected as shown below:

Claim 2, delete the structure shown, and insert therefor

--  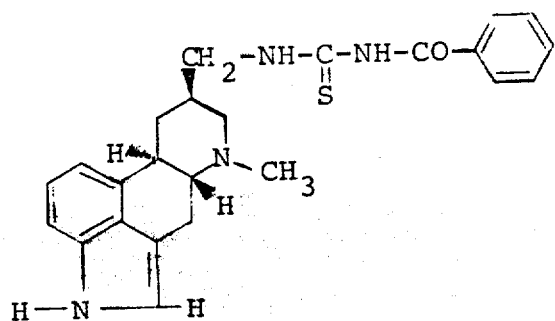  --

UNITED STATES PATENT AND TRADEMARK OFFICE
CERTIFICATE OF CORRECTION

PATENT NO. : 4,500,712
DATED : February 19, 1985
INVENTOR(S) : LUIGI BERNARDI ET AL Page 3 of 3

It is certified that error appears in the above-identified patent and that said Letters Patent is hereby corrected as shown below:

Claim 3, delete the structure shown, and insert therefor

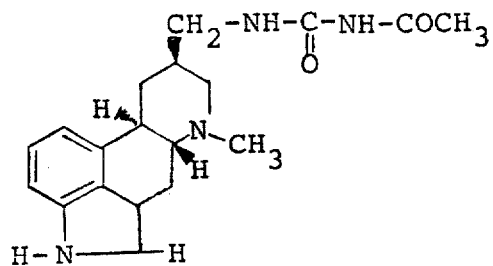

Signed and Sealed this

Sixteenth Day of September 1986

[SEAL]

Attest:

DONALD J. QUIGG

Attesting Officer

Commissioner of Patents and Trademarks